United States Patent [19]
Bakassian et al.

[11] 3,943,099
[45] Mar. 9, 1976

[54] PROCESS FOR STABILISING HALOGENATED VINYL RESINS

[75] Inventors: Georges Bakassian, Ste-Foy-les-Lyon; Michel Gay, Lyon; Marcel Lefort, Caluire, all of France

[73] Assignee: Rhone-Poulenc Textile, Paris, France

[22] Filed: Oct. 2, 1974

[21] Appl. No.: 511,263

[30] Foreign Application Priority Data
Oct. 5, 1973 France .............................. 73.35684

[52] U.S. Cl. .................... 260/45.75 E; 260/45.75 S
[51] Int. Cl.² ........................ C08K 3/16; C08K 5/58
[58] Field of Search ................ 260/45.75 E, 45.75 S

[56] References Cited
UNITED STATES PATENTS

| | | |
|---|---|---|
| 2,731,484 | 1/1956 | Best .................................. 260/45.75 |
| 2,752,325 | 6/1956 | Leistner et al. .................. 260/45.75 |
| 2,798,863 | 7/1957 | Tomka ............................... 260/45.75 |
| 3,067,166 | 12/1962 | Zaremsky ......................... 260/45.75 |
| 3,642,677 | 2/1972 | Brecker et al. .................. 260/45.75 |
| 3,655,613 | 4/1972 | Wowk ............................... 260/45.75 |
| 3,665,025 | 5/1972 | Wowk ............................... 260/45.75 |
| 3,715,333 | 2/1973 | Larkin ............................. 260/45.75 |

Primary Examiner—V. P. Hoke
Attorney, Agent, or Firm—Cushman, Darby & Cushman

[57] ABSTRACT

Halogenated vinyl resins are redendered less susceptible to yellowing on heating by the incorporation of stannic chloride as well as a diorgano-tin dimercaptide.

10 Claims, No Drawings

PROCESS FOR STABILISING HALOGENATED VINYL RESINS

The present invention relates to a process for stabilising halogenated vinyl resins, in particular polyvinyl chloride and its copolymers, in particular rendering them heat-resistant.

Many stabilisers for halogenated vinyl resins have been described in specialised literature. Amongst these stabilisers, the most effective have proved to be organo-stannic compounds, especially organo-tin mercaptides, described in, for example French Patent Nos. 1,055,906, 1,085,807 and 1,138,451, in particular saturated mercaptides, such as dibutyl and dioctyl-tin-bis-(isooctylmercaptoacetate). However, these compounds are not wholly satisfactory for some uses. In fact, in order to make it easier to handle the resins so as to increase the rate of production of various articles made of such resins, it is desired to process the resins at higher and higher temperatures. Such requirements, even with the best stabilisers, lead to disadvantages of which the main one is the appearance of yellowing. This yellow coloration is unacceptable for some applications, such as the production of transparent thin-walled articles. This is why attempts continue to develop stabilisers or mixtures of stabilisers which, whilst preventing yellowing, make it possible to handle vinyl resins for a few minutes at temperatures as high as possible, in particular from 180° to 230°C.

According to the present invention, there is provided a process for stabilising halogenated vinyl resins which comprises incorporating therein a diorgano-tin dimercaptide and stannic chloride as stabilisers.

The addition of stannic chloride makes it possible to delay the appearance of yellowing in halogenated vinyl resins stabilised by means of customary organo-tin mercaptides. This discovery, made when the resins are heated for a few minuted at a temperature above 180°C, could not have been foreseen, since the prior art teaches that the presence of a metal chloride, such as stannic chloride, accelerates the decomposition (dehydrochlorination) of polyvinyl chloride [see G. C. MARKS, J. L. BENTON and C. M. THOMAS: Advances in polymer science and technology, S.C.I. Monograph, 26, 204 (1967)].

In order to obtain good results when using the stabiliser mixture used in the present invention, the proportion by weight of stannic chloride relative to the overall weight of the stabilising mixture is suitably from 0.2% to 5%, preferably from 0.4% to 2.5% by weight.

The diorgano-tin mercaptides which are preferably used are products resulting from the condensation of a diorgano derivative of tetravalent tin, (i.e. a dialkyl-tin oxide or dichloro-dialkyl-stannane) with a monomercaptan or a polymercaptan which possesses one or more ester groups. The diorgano derivatives of tetravalent tin have the formulae: $R_2SnO$ or $R_2SnCl_2$ in which the R radicals, which may be identical or different, each represents a straight or branched alkyl group containing 1 to 10 carbon atoms.

The monomercaptans or polymercaptans which possess one or more ester groups may be esters of mercaptocarboxylic acids or $\alpha,\omega$-dimercapto-diesters.

The esters of mercaptocarboxylic acids have the formula:

$$HS - X - COOR' \qquad (I)$$

in which X represents a straight or branched alkylene group with 1 to 4 carbon atoms or a phenylene group, and R' is a hydrocarbon radical which is an alkyl or alkenyl group with at most 10 carbon atoms or a cycloalkyl or cycloalkenyl radical with 5 or 6 carbon atoms in the ring, or a phenylalkyl group, the alkyl part of which contains 1 to 4 carbon atoms.

The $\alpha,\omega$-dimercapto-diesters have the formula:

$$HS - X - COO - Y - OCO - X - SH \qquad (II)$$

in which X has the meaning given above and Y represents a straight or branched aliphatic divalent hydrocarbon radical with at most 10 carbon atoms, or a cycloaliphatic divalent hydrocarbon radical with 5 or 6 carbon atoms in the ring. The divalent radical Y can be saturated (i.e. it is an alkylene or cycloalkylene radical) or can possess one or two ethylenically and/or acetylenically unsaturated bonds. Y can also be a divalent radical which contains polysulphanediyl radicals and has the formula:

$$- Y^1 - S_x - Y^2 -$$

in which the various symbols represent:

$x$: an integer from 2 to 6; $Y^1$ and $Y^2$, which may be identical or different: each a divalent hydrocarbon radical, the free valencies of which are attached to carbon atoms devoid of aromatic character, this radical being a straight or branched alkylene group which has at most 6 carbon atoms and which is optionally substituted by one or more phenyl or alkylphenyl radicals, the alkyl substituent of the phenyl group having 1 to 6 carbon atoms; a cycloalkylene group with 5 or 6 carbon atoms in the ring; or a group of the formula $- Z^1 - S - Z^2 -$ in which the divalent radicals $Z^1$ and $Z^2$, which may be identical or different, represent straight or branched alkylene radicals with 1 to 6 carbon atoms.

The $\alpha,\omega$-dimercapto-diesters can be prepared by an esterification reaction employing a diol $HO - Y - OH$ and a mercaptocarboxylic acids $HS - X - COOH$, the various symbols having the meaning given above.

The mercaptocarboxylic acids are described in the literature. Amongst the mercaptocarboxylic acids, which may be used the following are exemplary: thioglycollic acid, $\beta$-mercaptopropionic acid, $\alpha$-, $\beta$- and $\gamma$-mercaptobutyric acids, $\beta$-, $\gamma$- and $\delta$-mercaptovaleric acids, thiolactic acid and thiosalicylic acid.

Amongst the diols $HO - Y - OH$, the following compounds may be mentioned by way of illustration: saturated diols such as propane-1,3-diol, butane-1,4-diol, pentane-1,5-diol, hexane-1,6-diol, octane-1,8-diol, butane-3,4-diol, pentane-1,4-diol, pinacol and 3-methyl-heptane-4,5-diol; unsaturated diols such as but-2-ene-1,4-diol, pent-2-ene-1,5-diol, hex-2-ene-1,6-diol, oct-2-ene-1,8-diol, but-1-ene-3,4-diol, pent-1-ene-3,4-diol, pent-2-ene-1,4-diol, hex-2-ene-1,5-diol, hept-3-ene-6,7-diol, oct-4-ene-3,6-diol, but-2-yne-1,4-diol, pent-2-yne-1,4-diol, hex-3-yne-2,5-diol, hexa-1,5-diene-3,4-diol, oct-4-yne-3,6-diol, octa-2,6-diene-4,5-diol and 3-methyl-hepta-2,6-diene-4,5-diol; and sulphur-containing diols possessing disulphide groups of the formulae:

$$HO - CH_2 - CH_2 - S - S - CH_2 - CH_2 - OH,$$

$$HO-CH_2-CH_2-S-CH_2-CH_2-S-S-CH_2-CH_2-S-CH_2-CH_2-OH,$$

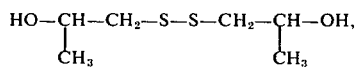

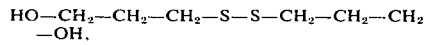

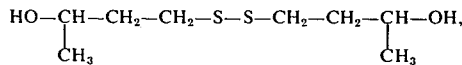

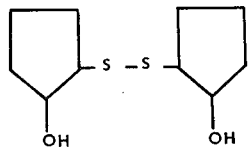

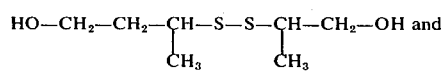

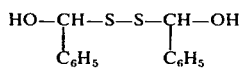

It is also possible to use sulphur-containing diols possessing a polysulphanediyl group, the formulae of which are derived from the formulae given above, replacing the disulphide group by a polysulphide group containing 2 to 6 sulphur atoms. These diols possessing a polysulphanediyl group generally consist of a mixture of varying proportions of sulphur-containing diols possessing a di-, tri-, tetra-, penta- or hexa-sulphide chain.

The sulphur-containing diols used to prepare the α, ω-dimercapto-diesters can be obtained easily either by controlled oxidation of mercaptoalcohols, or by reaction of halogenated alcohols with alkali metal or ammonium sulphides or polysulphides. Such methods are described in "Organic Chemistry of Bivalent Sulfur", volumes I and II E. REID, (1958). The reaction of a halogenated alcohol with an alkali metal or ammonium polysulphide leads to a mixture of dihydroxypolysulphides possessing a polysulphanediyl radical which contains 2 to 6 sulphur atoms.

The diorgano-tin mercaptides which result from the condensation of a diorgano derivative of tetravalent tin with a mercaptocarboxylic acid ester of the formula (I) have the general formula:

$$R_2Sn(S — X — COOR')_2 \quad (III)$$

Some of these mercaptides are described in French Patent No. 1,085,807 and in U.S. Pat. No. 2,641,596. Amongst the diorgano-tin dimercaptides, the following compounds may be mentioned by way of illustration: dibutyl-or dioctyl-tin bis-(isooctylmercaptoacetate), dimethyl-tin bis-(isooctylmercaptoacetate), dibutyl-tin bis-(butylmercapto acetate), dibutyl-tin bis-(butylmercaptopropionate), dimethyl-tin bis-(butylthiosalicylate), dibutyl-tin bis-(ethylmercaptovalerate), dibutyl-tin bis-(cyclohexenylmercaptoacetate) and dibutyl-tin bis-(phenylethylmercaptoacetate).

The diorgano-tin mercaptides which result from the condensation of a diorgano derivative of tetravalent tin with an α,ω-dimercapto-diester of the formula (II) consist essentially of groups of the formula:

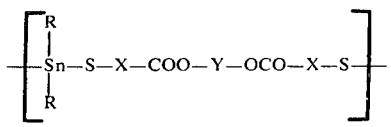

The number of groups (IV) present is generally from 1 to 5, and the dimercaptides can contain monomeric and dimeric forms of the formulae:

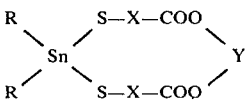

and

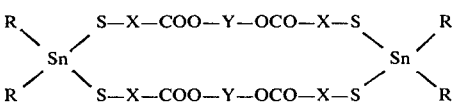

In such diorgano-tin dimercaptides the various symbols are preferably as follows:

R: an aklyl group with 1 to 10 carbon atoms,
X: a methylene or ethylene group,
R': an alkyl group with 1 to 10 carbon atoms, and
Y: an alkylene, alkenylene or alkynylene group with at most 10 carbon atoms, or a group of the formula $—Y_1 — S_x — Y_2 —$, in which $Y_1$ and $Y_2$ each represents an alkylene group with at most 6 carbon atoms and $x$ is an integer from 2 to 6.

The mixture for stabilising halogenated vinyl resins can comprise a mixture of the specified diorgano-tin dimercaptides. The mercaptides and the stannic chloride are generally mixed first, and then the mixture is introduced into the vinyl resin. Homogenisation of the halogenated vinyl composition is advantageously carried out on a malaxator It is also possible to incorporate the constituents of the stabilising mixture separately into the halogenated vinyl resin. It is also possible to introduce other stabilisers such as, for example, alkylthiostannoic anhyrides, diorgano-tin sulphides, other mercaptides and/or organo-stannic compounds which contain both mercapto groups and carboxylic acid groups bonded to the tin atom, into the halogenated vinyl resin. The addition of stannic chloride to these mixtures of stabilisers delays the appearance of yellowing in the resin.

For some uses, it can be advantageous to incorporate also an organo-tin trimercaptide of the formula $$R—Sn(S — X — COOR')_3,$$

various symbols having the meaning given above. The proportion of trimercaptide in the stabilising mixture is generally less than 10% of the total weight of stabilisers. The presence of stannic chloride in these mixtures here again delays the appearance of yellowing in the resin.

The mixture of stabilisers is generally introduced into the halogenated vinyl resin in an amount from 0.2 to 3% by weight based on the weight of the resin.

By "halogenated vinyl resins", as used herein, are meant, in accordance with traditional terminology in the art, polyvinyl chloride and vinyl chloride copolymers in which the portion originating from vinyl chloride predominates. Amongst the compounds which are suitable for copolymerisation with vinyl chloride, there may be mentioned vinyl esters such as vinyl acetate, vinyl bromide, vinyl fluoride and vinyl butyrate; vinyl ethers such as vinyl ethyl ether; acrylic acid and its derivatives such as ethyl acrylate, ethyl methacrylate, acrylonitrile and acrylamide; allyl compounds such as allyl chloride and allyl acetate; and ethylenic compounds such as ethylene, propylene and butadiene.

The addition of the stabilising mixture consisting of diorgano-tin dimercaptides and stannic chloride makes it possible, as has been stated, to delay the appearance of yellowing. Such an effect is particularly valuable in the production of transparent articles by means of extrusion or calendering techniques.

The following Examples further illustrate the present invention.

EXAMPLE 1

Various mixtures of stabilisers, comprising stannic chloride and di-(noctyl)-tin bis-(isooctylmercaptoacetate) in different proportions, are prepared.

Various samples based on polyvinyl chloride resin, having the following composition:

| | |
|---|---|
| Commercial polyvinyl chloride | 100 g |
| styrene/butadiene/methyl methacrylate terpolymer, used to provide impact strength | 10 g |
| ester of 1,3-butylene glycol and oxidised lignite wax, sold commercially as "Wax E" | 1 g |
| stabilising mixture | 1 g | are then prepared.

Each mixture is melted in a mixer possessing two rollers which rotate at the rate of 15 revolutions/minute and are heated to 180°C (Temperature maintained to within approximately 2°C). Samples are removed, the first after having been worked for 5 minutes on the calenders, and the following samples at 3 minute intervals thereafter. The coloration indices on the Gardner scale are noted with the aid of a Lovibond comparison disc. For comparison purposes, the results which are obtained when stannic chloride is not incorporated are included in the Table below.

The substantial improvement provided by stannic chloride can be seen.

| Gardner indices | DURATION OF HEATING AT 180°C., in minutes | | | | | |
|---|---|---|---|---|---|---|
| | 5 | 8 | 11 | 14 | 17 | 20 |
| Stabiliser A* SnCl₄ content : 0 | 2 | 3 | 4 | 4 | | |
| Stabiliser A SnCl₄ content : 0.5% | 0 | 0 | 0 | 1 | 2 | 3 |
| Stabiliser A SnCl₄ content : 0.7% | 0 | 0 | 0 | 1 | 1 | 2 |
| Stabiliser A SnCl₄ content : 0.9% | 0 | 0 | 0 | 1 | 1 | 2 |
| Stabiliser A SnCl₄ content 1% | 0 | 0 | 0 | 0 | 1 | 1 |
| Stabiliser A SnCl₄ content : 3% | 0 | 0 | 0 | | | |

*Composition of stabiliser A:
(octyl)₂Sn[—S—CH₂—COO(isooctyl)]₂ (100%)

EXAMPLE 2

Following the procedure described in Example 1, the Gardner indices of polyvinyl chloride resin stabilised with a mixture of stannic chloride and an organo-stannic compound having the following composition by weight: Dibutyl-tin-bis-(isooctylmercaptoacetate): 95% and butyl-trichloro-tin: 5% (Stabiliser B) are measured.

The results are given in the Table which follows.

| Gardner indices | DURATION OF HEATING AT 180°C. in minutes | | | | |
|---|---|---|---|---|---|
| | 5 | 8 | 11 | 14 | 17 |
| Stabiliser B SnCl₄ content : 0 | 0 | 0 | 1 | 2 | 2 |
| Stabiliser B SnCl₄ content : 1% | 0 | 0 | 0 | 0 | 1 |
| Stabiliser B SnCl₄ content : 2.5% | 0 | 0 | 0 | 0 | 1 |
| Stabiliser B SnCl₄ content : 5% | 0 | 0 | 0 | 0 | |

EXAMPLE 3

Following the procedure described in Example 1, the Gardner indices of polyvinyl chloride resin stabilised with a mixture of stannic chloride and stabiliser C, having the following composition, by weight:

| | |
|---|---|
| (octyl)₂Sn[—S—CH₂—COO—(isooctyl)]₂ | 88% |
| octyl — Sn[—S—CH₂—COO—(isooctyl)]₃ | 5% |
| (octyl)₂Sn—S—CH₂—CO— | 7% |

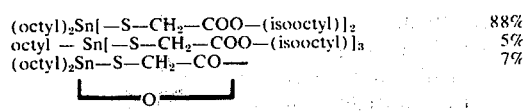

are measured.

The results are given in the Table which follows.

| Gardner indices | DURATION OF HEATING AT 180°C., in minutes | | | | | |
|---|---|---|---|---|---|---|
| | 5 | 8 | 11 | 14 | 17 | 20 |
| Stabiliser C SnCl₄ content : 0 | 0 | 1 | 1 | 2 | 3 | 3 |
| Stabiliser C SnCl₄ content : 0.6% | 0 | 0 | 0 | 1 | 1 | 2 |
| Stabiliser C SnCl₄ content : 0.8% | 0 | 0 | 0 | 0 | 1 | 2 |
| Stabiliser C SnCl₄ content : 1% | 0 | 0 | 0 | 0 | 0 | 1 |

EXAMPLE 4

The compound which results from the condensation of 2.1 mols of dibutyl-dichloro-tin (636 g.) with 1.6 mols of butene-diol bis-(mercaptoacetate) (378 g.) and 1 mol of isooctyl mercaptoacetate (206 g.) is used as the diorgano-tin dimercaptide. This mercaptide consists of the following groups:

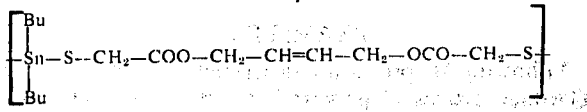

and

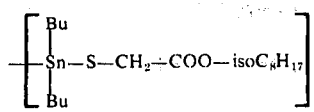

This dimercaptide is used in conjunction with stannic chloride to stabilise PVC. The Gardner indices of the stabilised resins are given in the Table which follows:

| Gardner indices | \multicolumn{7}{c}{DURATION OF HEATING AT 180°C, in minutes} |

| Gardner indices | 5 | 8 | 11 | 14 | 17 | 20 | 23 |
|---|---|---|---|---|---|---|---|
| Stabiliser D without any SnCl₄ | 0.5 | 1 | 2 | 2 | 2.5 | 3 | 3 |
| Stabiliser D SnCl₄ content : 1% | 0 | 0 | 0 | 0 | 0.5 | 0.5 | 0.5 |

We claim:

1. A process for stabilising a halogenated vinyl resin which comprises incorporating stannic chloride and a diorgano-tin dimercaptide into the resin, as stabilisers, the stannic chloride being present in an amount from 0.2% to 5% by weight based on the weight of the stabiliser mixture, the diorgano-tin dimercaptide being obtained by condensing
   a. a diorgano derivative of tetravalent tin selected from a dialkyl-tin oxide of formula $R_2SnO$, and a dichloro-dialkyl-stannane of formula $R_2SnCl_2$, in which each R radical which may be identical or different, represents a straight or branched alkyl group with up to 10 carbon atoms; with
   b. a mono- or poly-mercaptan containing one or more ester groups, selected from a mercaptocarboxylic acid ester of the formula:

HS — X — COOR' in which X represents a straight or branched alkylene group with up to 4 carbon atoms or a phenylene group, and R' represents an alkyl or alkenyl group with at most 10 carbon atoms, a cycloalkyl or cycloalkenyl group with 5 or 6 carbon atoms in the ring, or a phenylalkyl group, the alkyl part of which possesses 1 to 4 carbon atoms; and an α,ω-dimercapto-diester of the formula:

HS — X — COO — Y — OCO — X — SH in which X is as defined above and Y represents either a straight or branched aliphatic divalent hydrocarbon radical with at most 10 carbon atoms, or a cycloaliphatic divalent hydrocarbon radical with 5 or 6 carbon atoms in the ring, said radical optionally containing one or two ethylenic and/or acetylenic bonds.

2. Process according to claim 1 in which the diorgano-tin dimercaptide has the general formula:

$R_2Sn(S — X — COOR')_2$ in which R, X and R' are as defined in claim 1.

3. Process according to claim 2 in which the diorgano-tin dimercaptide is di-(n-octyl)-tin bis (isooctylmercapto-acetate or di-(n-butyl)-tin bis(isooctylmercapto-acetate).

4. Process according to claim 1 in which the diorgano-tin dimercaptide consists essentially of recurring units of the formula:

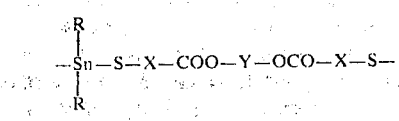

and, optionally, compounds of the formula:

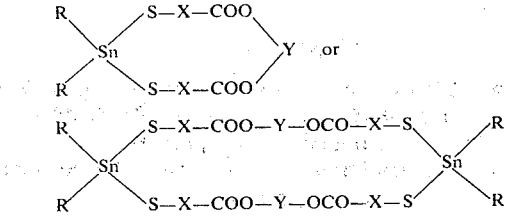

in which R, X and Y are as defined in claim 1.

5. Process according to claim 4 in which R represents a butyl radical, X represents —CH₂— and Y represents —CH₂—CH=CH—CH₂—.

6. Process according to claim 1 in which the stannic chloride is present in an amount from 0.4% to 2.5% by weight based on the weight of the stabiliser mixture.

7. Process according to claim 1 in which 0.2 to 3% by weight of the stabiliser mixture is incorporated.

8. Process according to claim 1 in which an organotin trimercaptide of the formula:

R—Sn (S—X—COOR')₃ in which R, X and R' are as defined in claim 1 is also incorporated.

9. Process according to claim 1 in which the halogenated vinyl resin is transparent.

10. Process according to claim 1 which comprises incorporating stannic chloride and a diorgano-tin dimercaptide of the formula:

$R_2Sn(S - X - COOR')_2$ or of recurring units of the formula:

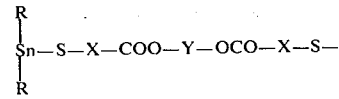

and, optionally, compounds of the formula:

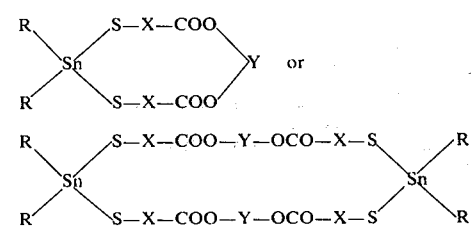

in which R represents an alkyl group with 1 to 6 carbon atoms, X represents a methylene or ethylene group, R' represents an alkyl group with 1 to 10 carbon atoms, and Y represents an alkylene, alkenylene or alkynylene group with at most 10 carbon atoms, said mixture being present in an amount from 0.2 to 3% by weight based on the weight of the resin.

* * * * *

UNITED STATES PATENT OFFICE
CERTIFICATE OF CORRECTION

Patent No. 3,943,099    Dated    March 9, 1976

Inventor(s)    Georges Bakassian, Michel Gay & Marcel Lefort

It is certified that error appears in the above-identified patent and that said Letters Patent are hereby corrected as shown below:

In the heading:

Change the name of the assignee from "Rhone-Poulenc Textile" to --Rhone-Poulenc S.A.--

Signed and Sealed this

Fourth Day of January 1977

[SEAL]

Attest:

RUTH C. MASON
*Attesting Officer*

C. MARSHALL DANN
*Commissioner of Patents and Trademarks*